(12) United States Patent
Cheng et al.

(10) Patent No.: US 10,722,705 B2
(45) Date of Patent: Jul. 28, 2020

(54) NERVE ELECTRICAL STIMULATION DEVICE

(71) Applicant: GiMer Medical Co., Ltd., New Taipei (TW)

(72) Inventors: Chan-Yi Cheng, New Taipei (TW); Chen-Tun Wu, New Taipei (TW)

(73) Assignee: GIMER MEDICAL CO., LTD., New Taipei (TW)

( * ) Notice: Subject to any disclaimer, the term of this patent is extended or adjusted under 35 U.S.C. 154(b) by 80 days.

(21) Appl. No.: 15/868,309

(22) Filed: Jan. 11, 2018

(65) Prior Publication Data

US 2018/0326205 A1  Nov. 15, 2018

(30) Foreign Application Priority Data

May 15, 2017 (CN) .......................... 2017 1 0337434

(51) Int. Cl.
*A61N 1/06* (2006.01)
*A61N 1/36* (2006.01)
*A61N 1/04* (2006.01)

(52) U.S. Cl.
CPC ............. *A61N 1/06* (2013.01); *A61N 1/0456* (2013.01); *A61N 1/36021* (2013.01); *A61N 1/048* (2013.01); *A61N 1/36034* (2017.08)

(58) Field of Classification Search
CPC .. A61N 1/36038; A61N 1/048; A61N 1/0456; A61N 1/36021; A61N 1/0541
See application file for complete search history.

(56) References Cited

U.S. PATENT DOCUMENTS

| | | | |
|---|---|---|---|
| 2003/0171787 A1* | 9/2003 | Money | A61N 1/36036 607/57 |
| 2011/0280424 A1* | 11/2011 | Takagi | G10L 21/02 381/317 |

* cited by examiner

*Primary Examiner* — Alyssa M Alter
(74) *Attorney, Agent, or Firm* — Muncy, Geissler, Olds & Lowe, P.C.

(57) ABSTRACT

A nerve electrical stimulation device includes an electrical stimulator and a magnetic electrode assembly. The electrical stimulator includes a housing, a circuit board, two first electrical connecting elements and a first magnetic unit. One end of each first electrical connecting element is connected to the circuit board. The magnetic electrode assembly includes a main body, two electrodes, a second magnetic unit and two second electrical connecting elements. The electrodes are disposed on a surface of the main body, and connected to the circuit board. The second magnetic unit is located corresponding to the first magnetic unit. The second electrical connecting elements pass through the main body and connected to the electrodes and the other ends of the first electrical connecting elements, respectively. The magnetic electrode assembly is detachably positioned at one side of the electrical stimulator by a magnetic attraction of the first and second electrical connecting elements.

11 Claims, 10 Drawing Sheets

NERVE ELECTRICAL STIMULATION DEVICE

CROSS REFERENCE TO RELATED APPLICATIONS

This Non-provisional application claims priority under 35 U.S.C. § 119(a) on Patent Application No(s). 201710337434.4 filed in People's Republic of China on May 15, 2017, the entire contents of which are hereby incorporated by reference.

BACKGROUND

Technology Field

The present disclosure relates to a nerve electrical stimulation device and, in particular, to a nerve electrical stimulation device with a detachable electrode assembly.

Description of Related Art

The electrical stimulators have a variety of uses. For example, the electrical stimulator has been widely used clinically to alleviate pains, such as cervical headache, occipital neuralgia, cervical injury, intercostal neuralgia . . . and other nerve-induced pains. The electrical stimulator have electrode pads to be attached on the skin surface of an individual, and can generate electrical stimulation signals through the electrodes to the related nerve area so as to provide electrical stimulation at different frequencies and intensities, thereby reducing the pain of the individual.

However, the pains often occurs in different parts of the individual. For example, the pain may occur in the head, shoulder, waist, or leg of an individual. On the other hand, the conventional electrical stimulators are usually unable to apply to different parts of an individual. This is because the electrode pads of the conventional electrical stimulator usually have a configuration conforming to a specific part of an individual and are fixed to an electrical stimulator, so that the electrode pads cannot be applied to different parts of individuals. This conventional design limits an electrical stimulator to be applied to relieve the pain of the same part of the individual. When the individual has the pain at different parts, the electrical stimulator with different configurations of electrode pads must be used additionally. Therefore, in order to stimulate different parts of the individual, the manufacturer should design corresponding shell or electrode pad configurations for different application parts. At the same time, users also need to purchase suitable electrical stimulators for different application parts. For manufacturers and consumers, it's an undesired cost or waste.

Therefore, it is an important subject to provide an electrical stimulation device that can be suitable for different parts of an individual, thereby saving the manufacturing and/or consumption cost.

SUMMARY

In view of the foregoing subject, an objective of this disclosure is to provide a nerve electrical stimulation device including an electrical stimulator in cooperation with detachable electrodes of different modes, which are designed for different parts of an individual, thereby saving the manufacturing and/or consumption cost.

To achieve the above objective, the present disclosure provides a nerve electrical stimulation device, which includes an electrical stimulator and a magnetic electrode assembly. The electrical stimulator includes a housing, a circuit board, at least two first electrical connecting elements and at least one first magnetic unit. The housing includes an accommodating space, and the circuit board and the first magnetic unit are disposed in the accommodating space. The first electrical connecting elements are disposed on the circuit board. One end of each first electrical connecting element is electrically connected to the circuit board, and the other end thereof exposes from the housing. The magnetic electrode assembly includes a main body, two electrodes, at least one second magnetic unit and at least two second electrical connecting elements. The electrodes are disposed on a surface of the main body opposite to the housing, and electrically connected to the circuit board. The second magnetic unit is disposed on the main body and located corresponding to the first magnetic unit. The second electrical connecting elements pass through the main body and are electrically connected to the electrodes, respectively. The second electrical connecting elements are electrically connected to the other ends of the first electrical connecting elements, respectively. The magnetic electrode assembly is detachably positioned at one side of the electrical stimulator by a magnetic attraction of the first electrical connecting elements and the second electrical connecting elements.

In one embodiment, the magnetic electrode assembly further includes at least one substrate connecting to the main body, and the electrodes are disposed at one side of the substrate opposite to the main body.

In one embodiment, the magnetic electrode assembly further includes at least one conductive paste disposed one side of the electrode away from the main body.

In one embodiment, the electrical stimulator outputs an electrical stimulation signal, the electrical stimulation signal is transmitted to the electrodes so as to generate an electric field between the electrodes to cover a target region, and an intensity of the electric field covering the target region is between 100 V/m and 1000 V/m.

In one embodiment, a frequency range of the electrical stimulation signal is between 200 KHz and 1000 KHz.

In one embodiment, each of the electrodes is a thin-film electrode.

In one embodiment, the first electrical connecting elements and the second electrical connecting elements form an electrical connecting route, which is different from a magnetic attraction route formed by the first magnetic unit and the second magnetic unit.

In one embodiment, the housing includes an upper housing and a lower housing. The lower housing has a depression portion, and the main body has a protrusion portion corresponding to the depression portion. The depression portion is engaged with the protrusion portion, and the second electrical connecting element penetrates through the protrusion portion of the main body.

In one embodiment, the main body has an opening, and the lower housing is partially protruded beyond the opening.

In one embodiment, the electrical stimulator further includes a prompt unit electrically connected to the circuit board and generating a prompt signal. The prompt unit includes a LED indicator, a vibration unit or a speaker.

As mentioned above, the nerve electrical stimulation device of this disclosure includes an electrical stimulator and a magnetic electrode assembly. The electrical stimulator and the magnetic electrode assembly are mechanically connected by the magnetic attraction of the first magnetic unit and the second magnetic unit so as to form a mechanical connection route, so that the magnetic electrode assembly can be detachably positioned at one side of the electrical stimulator. Accordingly, the same electrical stimulator can be cooperated with various modes of magnetic electrode assemblies for applying to different parts of an individual. This design can save the manufacturing and/or consumption cost. In addition, the electrical stimulator and the magnetic electrode assembly are coupled through the first electrical connecting elements and the second electrical connecting elements, so that the electrical signals generated by the circuit board can be transmitted to the electrodes so as to form an electrical transmission route, which is different from the mechanical connection route. Therefore, the mechanical design and the electrical transmission design are not interfered and affected by each other, thereby increasing the freedom of design.

BRIEF DESCRIPTION OF THE DRAWINGS

The disclosure will become more fully understood from the detailed description and accompanying drawings, which are given for illustration only, and thus are not limitative of the present disclosure, and wherein.

DETAILED DESCRIPTION OF THE DISCLOSURE

The present disclosure will be apparent from the following detailed description, which proceeds with reference to the accompanying drawings, wherein the same references relate to the same elements.

Figure 1A:
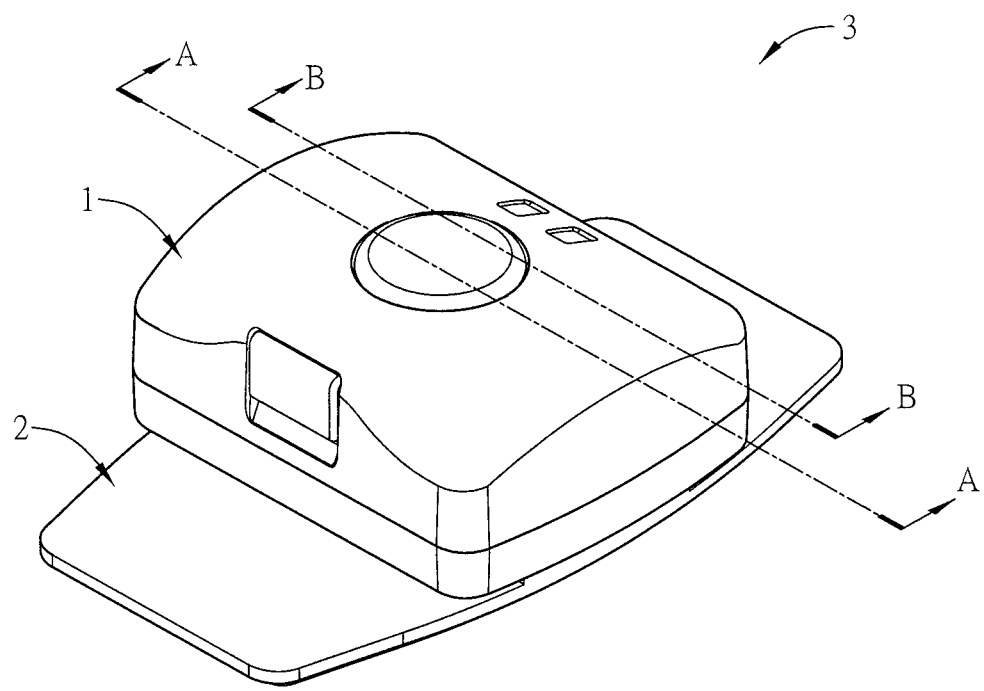
FIG. 1A is a schematic diagram showing a nerve electrical stimulation device according to an embodiment of the disclosure.
Figure 1B:
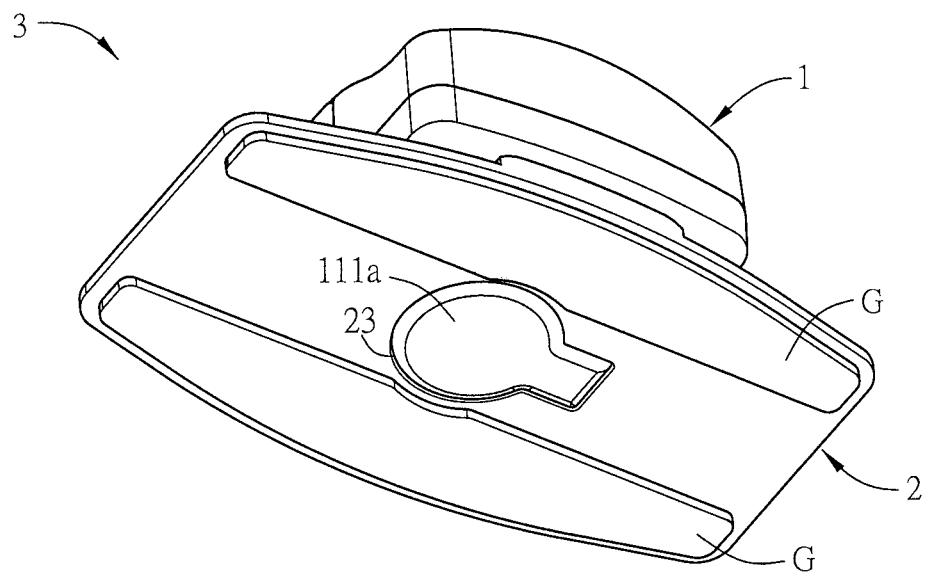
FIG. 1B is a schematic diagram showing another angle of the nerve electrical stimulation device of FIG. 1A.
Figure 1C:
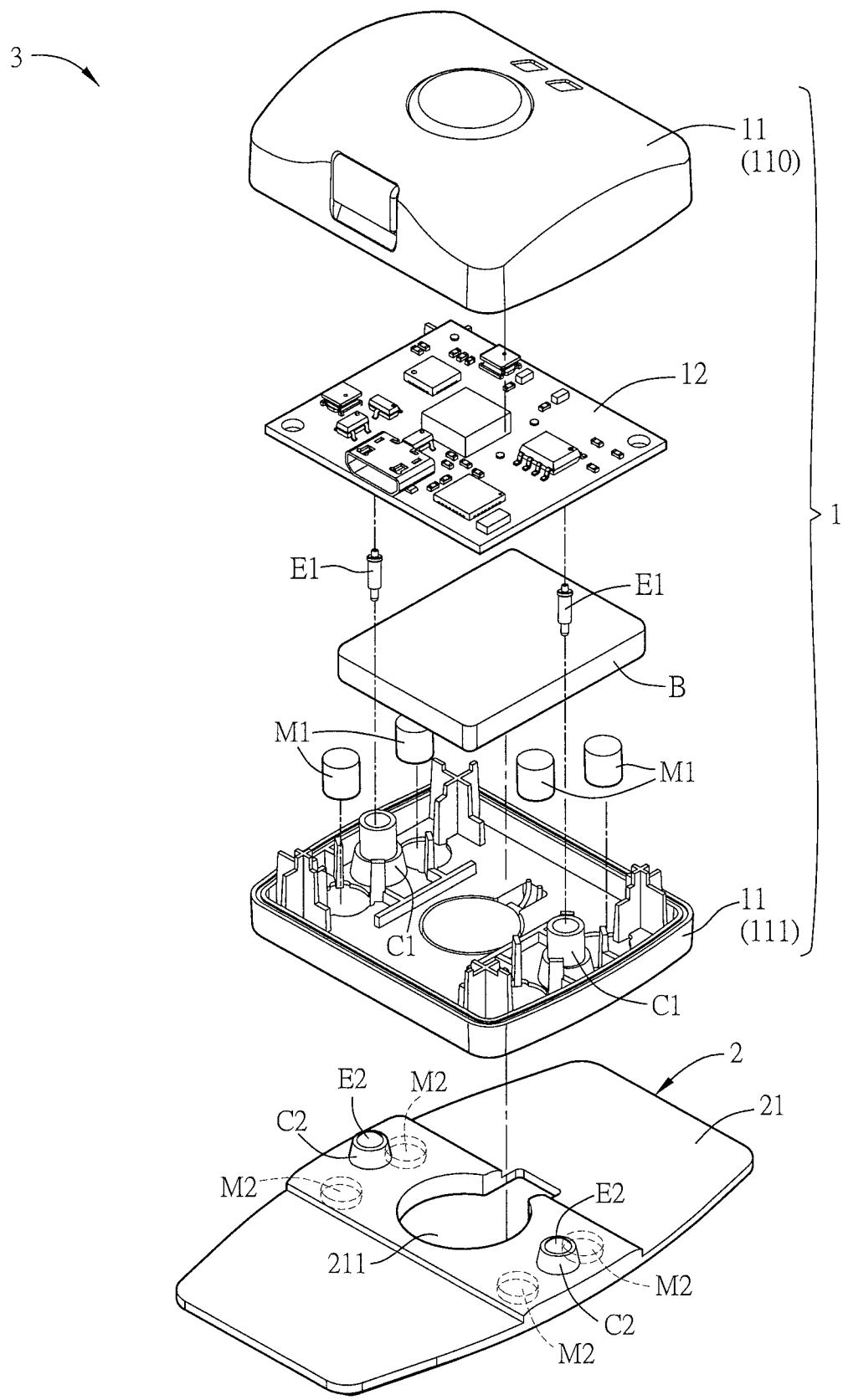
FIG. 1C is an exploded view of a part of the nerve electrical stimulation device of FIG. 1A.
Figure 1D:
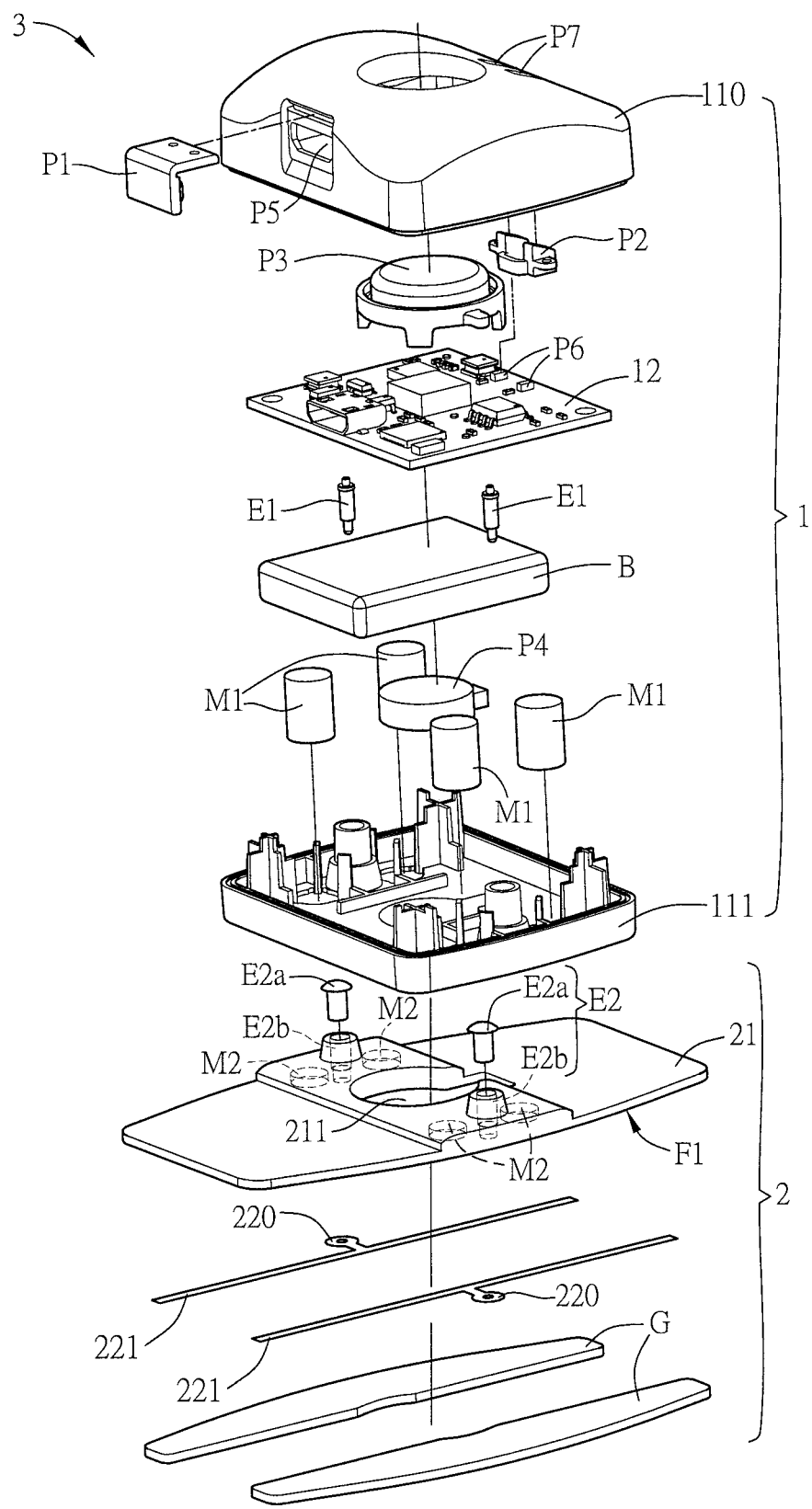
FIG. 1D is an exploded view of the nerve electrical stimulation device of FIG. 1A.
Figure 1E:
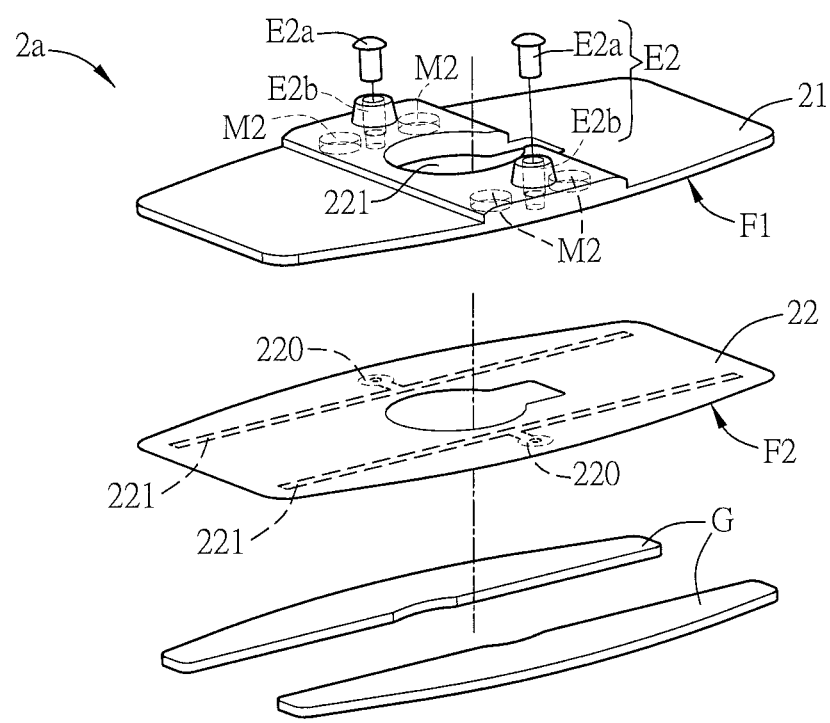
FIG. 1E is an exploded view of another magnetic electrode assembly of the nerve electrical stimulation device of FIG. 1A.
Figure 1F:
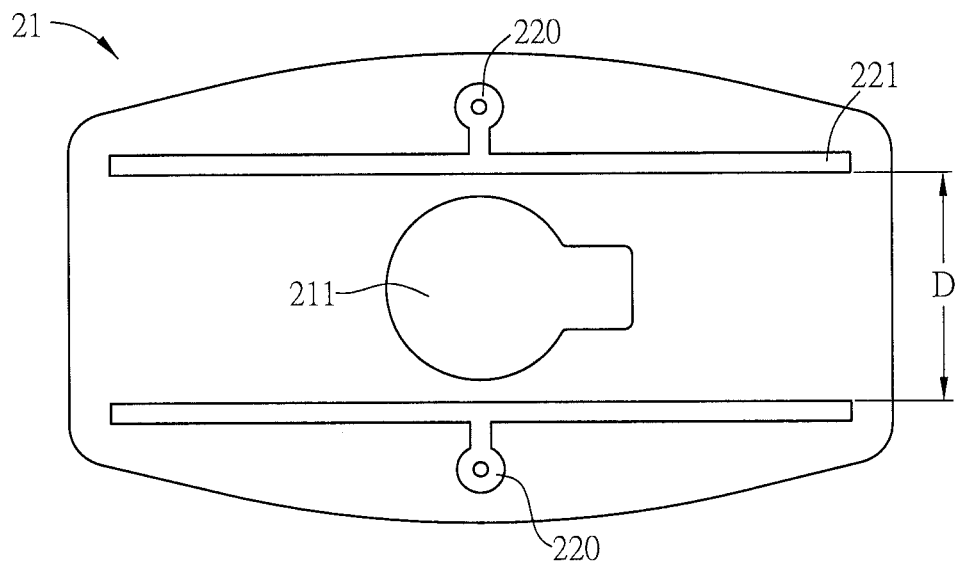
FIG. 1F is a schematic diagram showing the magnetic electrode assembly and the electrode of the nerve electrical stimulation device of FIG. 1A.
Figure 1G:
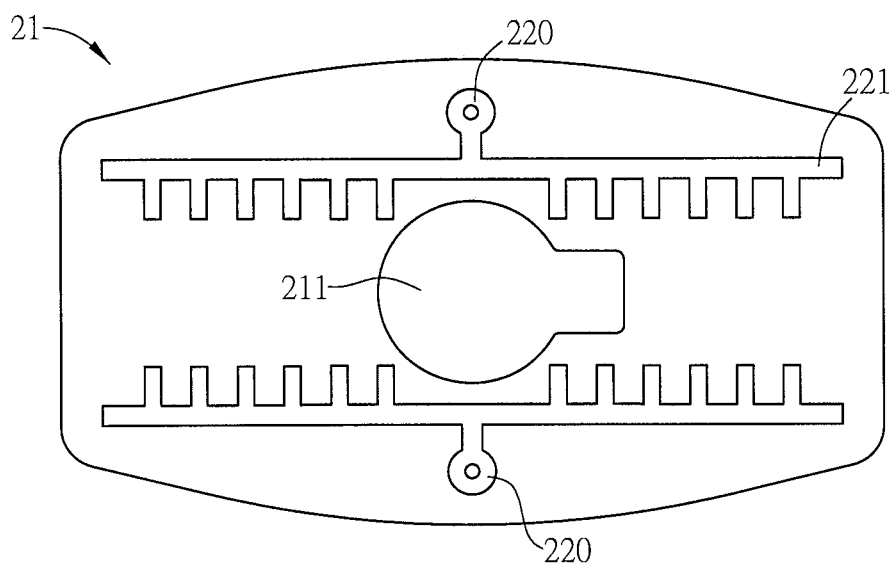
FIG. 1G is a schematic diagram showing the magnetic electrode assembly and another electrode of the nerve electrical stimulation device of FIG. 1A.
Figure 1H:
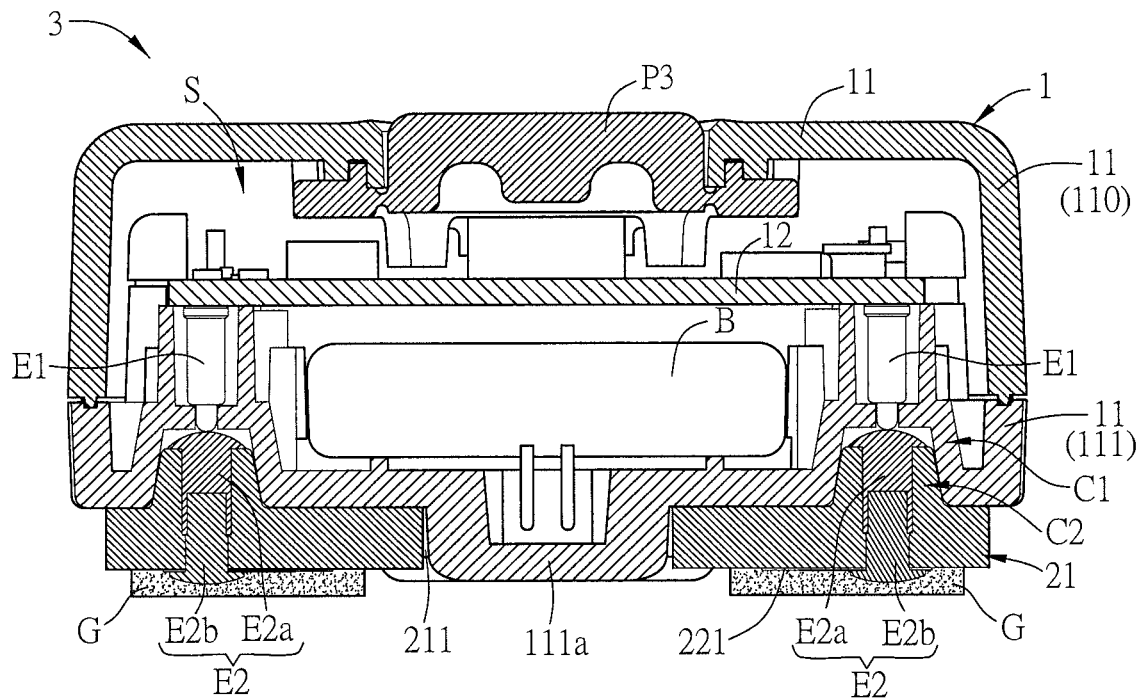
FIG. 1H is a sectional view of the nerve electrical stimulation device of FIG. 1A along the line A-A.
Figure 1I:
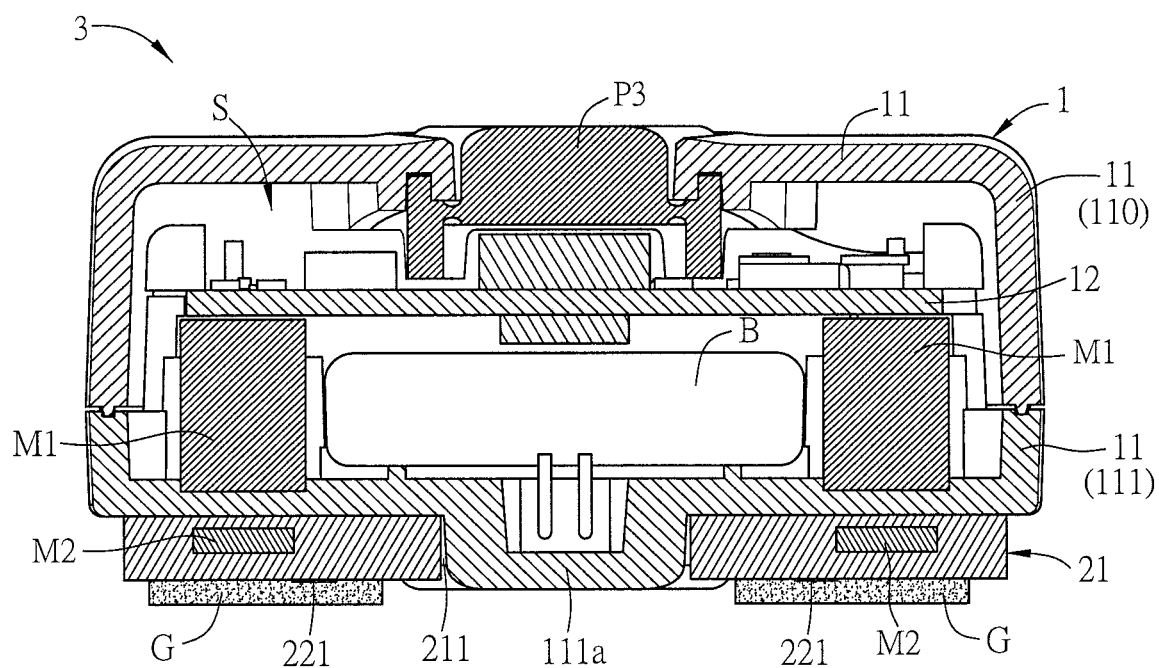
FIG. 1I is a sectional view of the nerve electrical stimulation device of FIG. 1A along the line B-B.
Figure 1J:
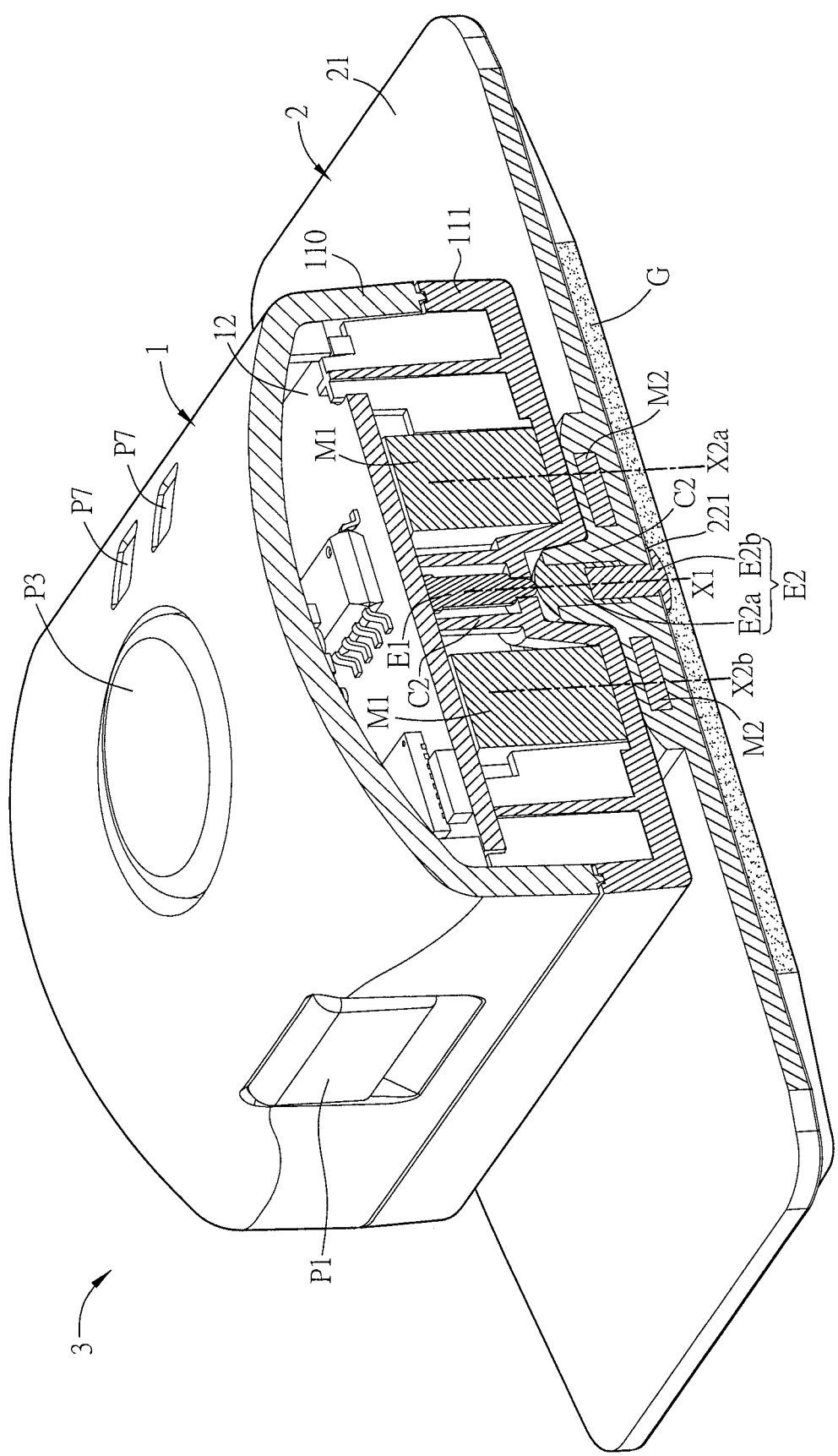
FIG. 1J is a perspective sectional diagram of the nerve electrical stimulation device of FIG. 1A.

FIG. 1A is a schematic diagram showing a nerve electrical stimulation device according to an embodiment of the disclosure. FIG. 1B is a schematic diagram showing another angle of the nerve electrical stimulation device of FIG. 1A. FIG. 1C is an exploded view of a part of the nerve electrical stimulation device of FIG. 1A. FIG. 1D is an exploded view of the nerve electrical stimulation device of FIG. 1A. FIG. 1E is an exploded view of another magnetic electrode assembly of the nerve electrical stimulation device of FIG. 1A. FIG. 1F is a schematic diagram showing the magnetic electrode assembly and the electrode of the nerve electrical stimulation device of FIG. 1A. FIG. 1G is a schematic diagram showing the magnetic electrode assembly and another electrode of the nerve electrical stimulation device of FIG. 1A. FIG. 1H is a sectional view of the nerve electrical stimulation device of FIG. 1A along the line A-A. FIG. 1I is a sectional view of the nerve electrical stimulation device of FIG. 1A along the line B-B. FIG. 1J is a perspective sectional diagram of the nerve electrical stimulation device of FIG. 1A.

As shown in FIGS. 1A and 1B, in this embodiment, a nerve electrical stimulation device 3 includes an electrical stimulator 1 and a magnetic electrode assembly 2. In this case, the nerve electrical stimulation device 3 is a transcutaneous electrical stimulator, which can be attached to the body surface or the skin of an individual by the magnetic electrode assembly 2 and provide the electrical stimulation to a target region. The transcutaneous electrical stimulator is not needed to be implanted into the body or skin of an individual. For example, the applied electrical stimulation can treat the shallow nerves under the surface by 10 mm or less so as to reduce the pain or other symptoms of the individual. Different from the general muscle electrical stimulation device, the nerve electrical stimulation device 3 of this embodiment applies the electrical stimulation to the nerves instead of muscles. When performing the nerve electrical stimulation, the two electrodes of the magnetic electrode assembly 2 are closer, and the distance between two electrodes is between 5 mm and 35 mm. The two electrodes can be a negative electrode and a positive electrode, or a working electrode and a reference electrode. For example, the working electrode outputs the electrical stimulation signal, and the reference electrode outputs a DC voltage signal of a fixed voltage level. However, the negative and positive electrodes of the general muscle electrical stimulation device are farther. In general, the distance between the negative and positive electrodes of the general muscle electrical stimulation device is related to the length of the muscle to be stimulated and is generally 3~5 cm or farther.

As shown in FIG. 1C, the electrical stimulator 1 is disposed at the top half of the electrical stimulation device 3. The electrical stimulator 1 includes a housing 11, a circuit board 12, at least two first electrical connecting elements E1, and at least one first magnetic unit M1. The housing 11 is formed by an upper housing 110 and a lower housing 111, which are made by plastics, composite materials, or composite metals. In practice, the housing 11 is integrally formed as one piece by injection molding or assembled by several parts. The upper housing 110 and the lower housing 111 are assembled to form an accommodating space S (see FIG. 1H) for accommodating most components of the electrical stimulator 1, such as the circuit board 12, the first electrical connecting elements E1, the first magnetic unit M1, and others. In addition, the magnetic electrode assembly 2 is disposed at the bottom half of the electrical stimulation device 3 and connected to the lower housing 111 of the electrical stimulator 1. The magnetic electrode assembly 2 includes a main body 21, two electrodes 221 (see FIG. 1D), at least one second magnetic unit M2, and at least two second electrical connecting elements E2.

The circuit board 12 is disposed in the accommodating space S and integrates most electronic components (e.g. the processing unit, control unit, memory unit, and the likes) or the transmission interfaces. The circuit board 12 can be a printed circuit board (PCB), such as the rigid printed circuit board (RPCB). Besides, the circuit board 12 can optionally be a multilayer PCB or high density interconnection (HDI) PCB according to the electronic properties and anti-EMI properties of the circuit board 12 and/or the utility of the accommodating space S. The electrical stimulation signal generated by the electrical stimulator 1 can be transmitted to the electrodes of other components through the circuit board 12, so that the electrical stimulation device 3 can provide the electrical stimulation to the target region of the individual.

Figure 2:
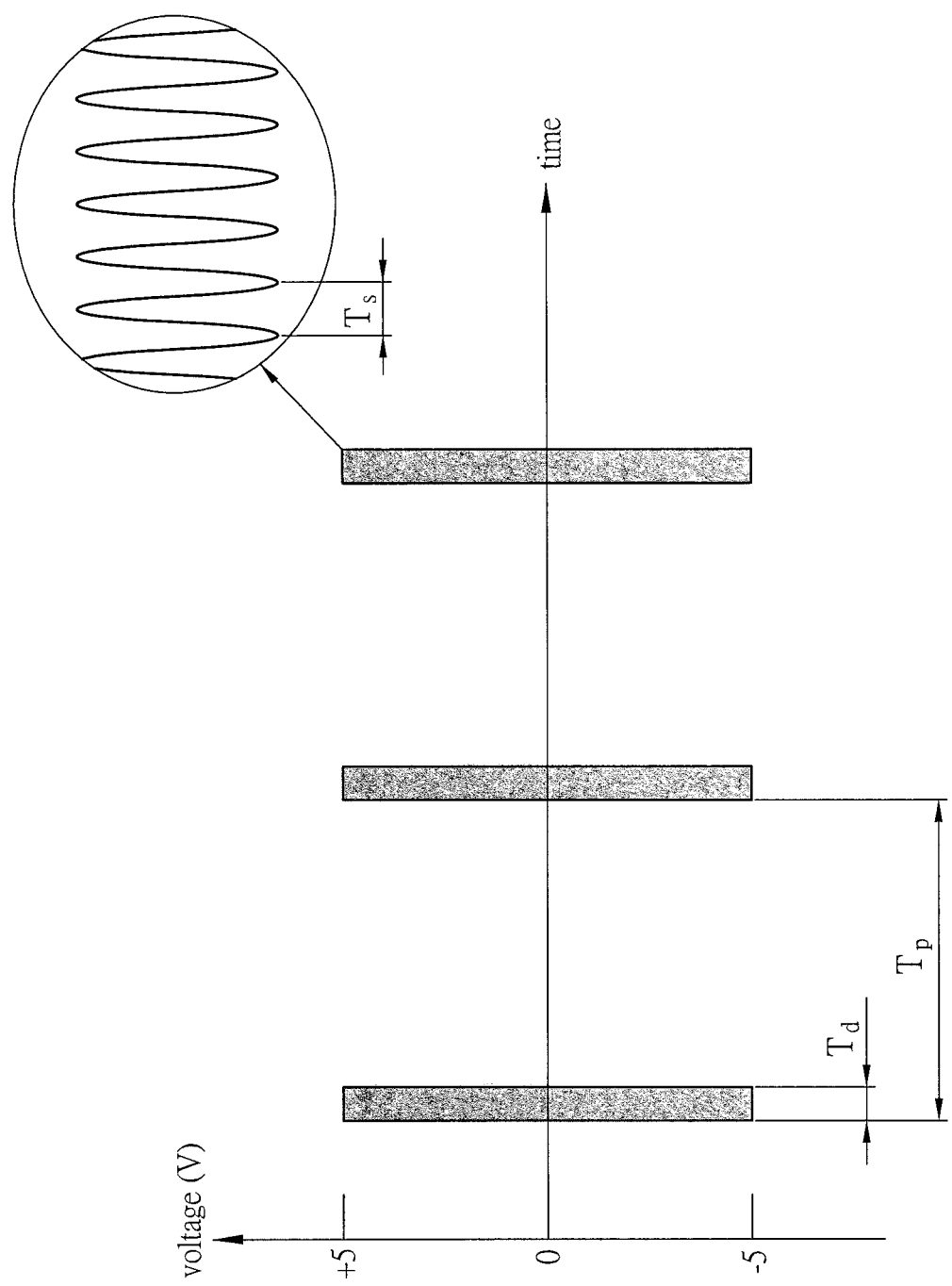
FIG. 2 is a schematic diagram showing the electrical stimulation signal of the nerve electrical stimulation device of FIG. 1A, wherein the electrical stimulation signal is a high-frequency pulse signal.

Referring to FIG. 2, the electrical stimulation signal outputted by the electrical stimulator 1 can be a continuous sine wave, continuous triangular wave or high frequency electrical stimulation signal, and the frequency thereof is between 200 KHz and 1000 KHz. In this embodiment, the frequency of the electrical stimulation signal is, for example, 500 KHz. When the electrical stimulation signal is a high frequency electrical stimulation signal, a pulse cycle time Tp may include a plurality of pulse signals and at least one rest period. A pulse cycle time is a reciprocal of the pulse repetition frequency (or pulse frequency), which is 0~1 KHz, and preferably is 0.1~100 Hz or 0.2~20 Hz. In this embodiment, the pulse repetition frequency of the electrical stimulation signal is 2 Hz. In addition, the duration time Td of a plurality of pulses in the pulse cycle time is 1~250 ms, and preferably 10~100 ms. In this embodiment, the frequency of the high frequency electrical stimulation signal is 600 KHz (the stimulation cycle time Ts is about 1.67 μs), and the duration time Td of the pulses is 25 ms.

In practice, the electrical stimulator 1 can be optionally driven by a constant voltage mode or a constant current mode. When the electrical stimulator 1 is driven by a constant voltage mode, the voltage of the outputted high frequency electrical stimulation signal is a constant value. When the electrical stimulator 1 is driven by a constant current mode, the current of the outputted high frequency electrical stimulation signal is a constant value. For example, a 10V AC voltage is applied in the constant voltage mode, so that the voltage of the high frequency electrical stimulation signal is between −10V and 10V. Preferably, the voltage of the high frequency electrical stimulation signal is between −5V and 5V, and the pulse waveform is a sine wave AC voltage. In the constant current mode, the current of the high frequency electrical stimulation signal is between 2 mA and 50 mA, and is preferably between 4 mA and 30 mA. In other embodiments, the pulse waveform can be a triangle wave or a square wave.

The components of the magnetic electrode assembly 2 and the relations thereof will be further described hereinafter.

Referring to FIGS. 1D, 1F and 1I, the main body 21 of the magnetic electrode assembly 2 is made of rubber, silicone or other flexible materials, so that the main body 21 is flexible and can be easily attached to different parts of the individual. In other aspects, the main body 21 can be made of an adhesive material, or an adhesive layer can be coated on the lower surface F1 of the main body 21. The adhesive layer can be made of ISO-10993 and ISO-14155 rubber based or silicone based medical-level glue. Accordingly, the magnetic electrode assembly 2 can be directly attached to the body surface of the individual. The two electrodes 221 is electrically connected to the circuit board 12, and the connection thereof will be described hereinafter. In this embodiment, the two electrodes 221 can be thin-film electrodes, which is formed by printing or spraying a conductive material (e.g. a silver paste) on a surface F1 of the main body 21 corresponding to the housing 11. The surface F1 is the lower surface of the main body 21 as shown in FIG. 1D, and is facing the user in operation. The thickness of the electrodes 221 is between 0.01 mm and 0.30 mm. As shown in FIG. 1F, the electrodes 221 of this embodiment is distributed in a pattern, such as two parallel bars. The distance D between the two electrodes 221 (along the main axis) can be between 5 mm and 35 mm, and this disclosure is not limited. The thickness and pattern of the electrodes 221 can be modified based on the actual requirement. In other embodiments, as shown in FIG. 1G the electrodes 221 can be two parallel comb patterns.

FIG. 1E is an exploded view of another magnetic electrode assembly 2a of the nerve electrical stimulation device. In this aspect, the components of the magnetic electrode assembly 2a and the connections thereof are mostly the same as those of the above-mentioned magnetic electrode assembly 2. Different from the magnetic electrode assembly 2, the magnetic electrode assembly 2a further includes a substrate 22 disposed on a surface F1 of the main body 21 opposite to the housing 11 (under the main body 21 as shown in FIG. 1D) and connected to the main body 21, for example, by adhering. The substrate 22 can be a plastic thin plate. In this aspect, the two electrodes 221 are disposed on a surface F2 of the substrate 22 opposite to the main body 21 (under the substrate 22 as shown in FIG. 1D), and the surface F2 is facing the user in operation.

Referring to FIGS. 1D and 1E, when operating the nerve electrical stimulation device 3, the lower surface of the main body 21 is applied with a conductive gel G. In other words, the conductive gel G is disposed on the attaching surfaces of the electrodes 221 away from the main body 21, and each electrode 221 is configured with one conductive gel G. The conductive gel G has adhesion ability so that the electrode patch 22 can be attached to the body surface or skin of the individual. In addition, the configuration of the conductive gel G can decrease the contact resistance between the electrode 221 and the body surface of the individual, and the current provided by the electrodes 221 can be evenly applied to the attached body surface area. This can prevent unstable stimulation and increase the comfort when using the nerve electrical stimulation device 3. Furthermore, two sides of the conductive gel G both have adhesion ability, and the adhesion ability of two sides of the conductive gel G can be different. For example, one side of the conductive gel G bonding to the electrode 221 has higher adhesion ability, and the other side of the conductive gel G (for contacting the body surface of the individual) has lower adhesion ability. Accordingly, when operating the nerve electrical stimulation device 3, the electrode 221 and the conductive gel G can be tightly bonded to each other when repeatedly attaching the main body 21 to the body surface of the individual. This configuration can reduce the risk of detachment of the electrode 221 and the conductive gel G. When removing the magnetic electrode assembly 2 from the body surface of the individual, the user will not be hurt. In addition, since the main body 21 is flexible, the magnetic electrode assembly 2 can fit the shape or curvature of the target region of the body surface of the individual when attaching the electrical stimulation device 3 on the body surface of the individual through the conductive gel G. Thus, the electrical stimulation device 3 can be firmly attached on the target region.

Referring to FIGS. 1D and 1I, the first magnetic unit M1 of the magnetic electrode assembly 2 is disposed in the accommodating space S (e.g. between the circuit board 12 and the housing 11). To be noted, the first magnetic unit M1 of this embodiment is disposed under the circuit board 12. In other embodiments, the first magnetic unit M1 can be disposed at any place instead of the place under the circuit board 12, and the first magnetic unit M1 and the second magnetic unit M2 (see FIG. 1I) are correspondingly disposed in the electrical stimulator 1 and the main body 21 of the magnetic electrode assembly 2, respectively, so that the electrical stimulator 1 and the magnetic electrode assembly 2 can magnetically attract each other through the two magnetic units. In this embodiment, the magnetic electrode assembly 2 includes at least one first magnetic unit M1 and at least one second magnetic unit M2, and the amount of the first magnetic units M1 can be the same as or different from the amount of the second magnetic units M2. In this embodiment, the magnetic electrode assembly 2 includes four first magnetic unit M1 and four corresponding second magnetic unit M2.

As shown in FIGS. 1D and 1I, the four first magnetic units M1 are uniformly and horizontally disposed around the periphery of the vibration unit P4 and located between the circuit board 12 and the lower housing 111. The four second magnetic units M2 are disposed in the main body 21 and located around the opening 211 of the main body 21. In this embodiment, for example, the second magnetic units M2 are embedded in the main body 21. Of course, the second magnetic units M2 can be disposed protruding on the main body 21 or adhered to the main body 21, and this disclosure is not limited. Each first magnetic unit M1 can be disposed on the extending direction of the long axis of the corresponding second magnetic unit M2, so that the first magnetic unit M1 and the second magnetic unit M2 can magnetically attract each other. Accordingly, the magnetic electrode assembly 2 can be detachably positioned at one side of the electrical stimulator 1 by the magnetic attraction of the first magnetic unit M1 and the second magnetic unit M2.

In another embodiment, the amounts and positions of the first magnetic units M1 and the second magnetic units M2, and the magnetic material of the second magnetic units M2 can be modified based on the actual requirement. This disclosure is not limited. Any embodiment that allows the electrical stimulator 1 and the magnetic electrode assembly 2 to magnetically attract each other by the first magnetic units M1 and the second magnetic units M2 and allows the magnetic electrode assembly 2 to be detachably positioned at one side of the electrical stimulator 1 is acceptable.

Referring to FIGS. 1B, 1H and 1I, in this embodiment, a protruding structure 111a is formed on the lower housing 11 of the electrical stimulator 1 corresponding to the opening 211 of the main body 21. After assembling the magnetic electrode assembly 2 to the electrical stimulator 1, the protruding structure 111a of the lower housing 11 can protrude beyond the opening 211 of the main body 21. Accordingly, the magnetic electrode assembly 2 can be firmly disposed on the electrical stimulator 1, and the magnetic electrode assembly 2 can be aligned to the electrical stimulator 1.

In more detailed, the first magnetic units M1 and the second magnetic units M2 can be made of spontaneous magnetic material or magnetic conductive material. The spontaneous magnetic material is, for example, an alloy including TbFe, GdCo, DyNi, NdFeB, ferrite or intermetallic compounds. The magnetic conductive material includes, for example, Co—Ni—Cr, Co—Cr—Ta, Co—Cr—Pt, or Co—Cr—Pt—B. The spontaneous magnetic material can provide magnetic force without additional magnetic field, but the magnetic conductive material must be induced by a magnetic field (e.g. around a magnet) to generate the magnetic force. The materials of first magnetic units M1 and the second magnetic units M2 are not limited to be the spontaneous magnetic material or the magnetic conductive material. In other words, the first magnetic units M1 and the second magnetic units M2 can both be made of spontaneous magnetic material, or one of the first magnetic units M1 and the second magnetic units M2 is made of spontaneous magnetic material, and the other one thereof is made of magnetic conductive material. Any configuration that allows the first magnetic units M1 and the second magnetic units M2 to magnetically attract each other so as to bond the electrical stimulator 1 to the magnetic electrode assembly 2 is acceptable.

Referring to FIGS. 1D and 1H, two first electrical connecting element E1 are disposed on the circuit board 12. The circuit board 12 includes a control unit C for outputting an electrical stimulation signal. One end of each first electrical connecting element E1 is electrically connected to the circuit board 12, and the other end thereof exposes from the housing 11. The magnetic electrode assembly 2 further includes at least two second electrical connecting elements E2. The second electrical connecting elements E2 pass through the main body 21 and are electrically connected to the electrodes 221, respectively. The second electrical connecting elements E2 are electrically connected to the other ends of the first electrical connecting elements E1, respectively. In this embodiment, the first electrical connecting element E1 can be an elastic pin (e.g. a pogo pin), so that the other end thereof can keep a certain collapse margin when contacting with the female rivet E2a of the second electrical connecting element E2, thereby absorbing the manufacturing tolerances or assembling errors of the magnetic electrode assembly 2 and the electrical stimulator 1 and thus increasing the convenience of manufacturing and assembling. The second electrical connecting element E2 can be formed by assembling a male rivet E2b and a female rivet E2a.

Referring to FIG. 1H, the lower housing 111 of the housing 11 includes at least one depression portion C1. The lower housing 111 is located at the bottom of the housing 11, which is facing the magnetic electrode assembly 2 or facing the target region of the user in operation. On the other hand, one side of the main body 21 facing the electrical stimulator 1 (away from the target region of the user in operation) is configured with a protrusion portion C2 corresponding to the depression portion C1. The protrusion portion C2 has a through hole, and the second electrical connecting element E2 passes through the through hole. When the magnetic electrode assembly 2 is assembled with the electrical stimulator 1, the protrusion portion C2 and the depression portion C1 are engaged with each other. Accordingly, the configuration of the depression portion C1 and the protrusion portion C2 can further align the electrical stimulator 1 and magnetic electrode assembly 2. As mentioned above, one end of each first electrical connecting element E1 is electrically connected to the circuit board 12, and the other end of the first electrical connecting element E1 is protruded beyond an opening of the depression portion C1. The second electrical connecting element E2 passes through the through hole of the protrusion portion C2.

As shown in FIGS. 1F and 1G, the protrusion portion C2 of the main body 21 has a through hole, and the electrode 221 is configured with an electrode conductive hole 220 corresponding to the through hole. The electrode conductive hole 220 can be made of conductive material and integrally formed with the electrode 221. Accordingly, one end of the male rivet E2b can pass through the through hole of the main body 21 and the electrode conductive hole 220 of the electrode patch 22. This structure can form an electrical connecting route through the circuit board 12, the first electrical connecting element E1, the second electrical connecting element E2 and the electrode 221, and the electric stimulation signal outputted from the circuit board 12 of the electrical stimulator 1 can be transmitted to the target region (to-be-treated region) of the individual through the first electrical connecting element E1, the second electrical connecting element E2 and the electrode 221.

When the protrusion portion C2 is engaged with the depression portion C1 (the magnetic electrode assembly 2 is assembled with the electrical stimulator 1), the female rivet E2a of the second electrical connecting element E2 can contact to the other end of the first electrical connecting element E1, thereby electrically connecting the second electrical connecting element E2 to the first electrical connecting element E1. Then, after the circuit board 12 of the electrical stimulator 1 outputs an electrical stimulation signal, it can be electrically connected with the electrode 221 through the first electrical connecting element E1 and the second electrical connecting element E2 (the male rivet E2b and the female rivet E2a). However, in other embodiments, the electrode patch 22 may not be configured with the electrode conductive hole 220, so that one end of the male rivet E2b directly passes through the main body 21 and contacts with the electrode 221, and the other end thereof is also engaged and electrically connected with the female rivet E2a. In this case, the circuit board 12 and the electrode 221 can still be electrically connected with each other.

Accordingly, the electrical stimulation signal outputted from the circuit board 12 of the electrical stimulator 1 can be transmitted to the two electrodes 221 through the above-mentioned electrical connecting route, thereby generating an electric field between the two electrodes 221 to cover the target region. An intensity of the electric field applied to the skin or covering the target region is between 100 V/m and 1000 V/m. The applied electric field can affect the nerve conduction (e.g. block or reduce the nerve conduction) so as to relieve pains or inhibit physiological signal transmission via nerves.

Referring to FIG. 1J, the electrical connecting route formed by the first electrical connecting element E1 and the second electrical connecting element E2 substantially forms an axial direction X1 perpendicular to the main body 21. Besides, the magnetic attraction routes formed by the first magnetic units M1 and the second magnetic units M2 substantially form the axial directions X2a and X2b, respectively, perpendicular to the major plane of the main body 21. To be noted, the axial direction X1 is not the axial direction X2a or X2b. In other words, the electrical connecting route formed by the first electrical connecting element E1 and the second electrical connecting element E2 is different from the magnetic attraction routes formed by the first magnetic units M1 and the second magnetic units M2. Accordingly, the electrical stimulator 1 and the magnetic electrode assembly 2 can be conducted through the first electrical connecting element E1 and the second electrical connecting element E2, so that the electrical signals generated by the circuit board 12 can be transmitted to the electrodes so as to form the electrical transmission route. The electrical transmission route is different from the mechanical connection route. Therefore, the mechanical design and the electrical transmission design are not interfered and affected by each other, thereby increasing the freedom of design.

In addition, the electrical stimulator 1 is disposed in the accommodating space S, and a battery B or a power source module can be configured for providing electric power to the circuit board 12. The processing unit or control unit of the circuit board 12 can control an optimum output of the battery B based on the requirement of electric stimulation. For example, the power output will be reduced in a standby mode, so that the electrical stimulation device 3 can have a longer using time or standby time. Thus, the user does not need to charge the electrical stimulation device 3 frequently, thereby making the operation of the electrical stimulation device 3 more comfortable. Referring to FIG. 1D, the electrical stimulator 1 further includes a waterproof cover P1, a light guiding bar P2, a button P3, a vibration unit P4, a USB interface P5, two LED indicators P6, and two light guiding holes P7. Besides, the housing 11 of the electrical stimulator 1 can also be made of a waterproof material for preventing the invasion of water or moisture.

The battery B of the nerve electrical stimulation device 3 can be charged via the USB interface P5, thereby making the operation of the electrical stimulation device 3 more comfortable. After finishing the charge of battery B, the waterproof cover P1 can be put on to correspondingly cover the opening of the USB interface P5. Besides, the battery B of the nerve electrical stimulation device 3 can be used to perform the bidirectional data transmission. For example, the detailed electrical stimulation parameters can be transmitted to an external device, or an updated firmware setup parameters can be transmitted from an external device to change the original setups of the output electrical stimulation signals. After finishing the data transmission, the waterproof cover P1 can be put on to correspondingly cover the opening of the USB interface P5. This configuration can prevent the water or dusts from entering the electrical stimulator 1 through the opening, thereby protecting the circuit board 12 and other electrical components and thus maintaining the lifetime of the product.

In this embodiment, the vibration unit P4 of the electrical stimulator 1 can function as a prompt unit for reminding the user about the operation status of the nerve electrical stimulation device 3. In practice, the prompt unit of the electrical stimulator 1 can be a LED indicator, a vibration unit, a speaker, or their combination, and this disclosure is not limited. In this embodiment, one vibration unit P4 and two LED indicators P6 are provided. The light guiding bars P2 are provided to guide the light emitted from the LED indicators P6 from the accommodating space S (see FIG. 1H) to the outside of the housing 11 via the two light guiding holes P7 of the upper housing 110, so that the user can easily observe the light. The vibration unit P4 is electrically connected to the circuit board 12 and generates a prompt signal. When the nerve electrical stimulation device 3 is starting to operate, the vibration unit P4 can generate a vibration and the LED indicators P6 can output a flashing light, so that the user can be announced that the nerve electrical stimulation device 3 is going to perform an electrical stimulation operation. In brief, the user can realize the operation status or operation mode of the nerve electrical stimulation device 3 according to the prompt signal generated by the prompt unit P4. The button P3 is disposed on the circuit board 12 and is exposed from the topmost part of the housing 11, so that the user can easily and rapidly control to turn on, turn off, or switch operation mode of the nerve electrical stimulation device 3.

Figure 3:
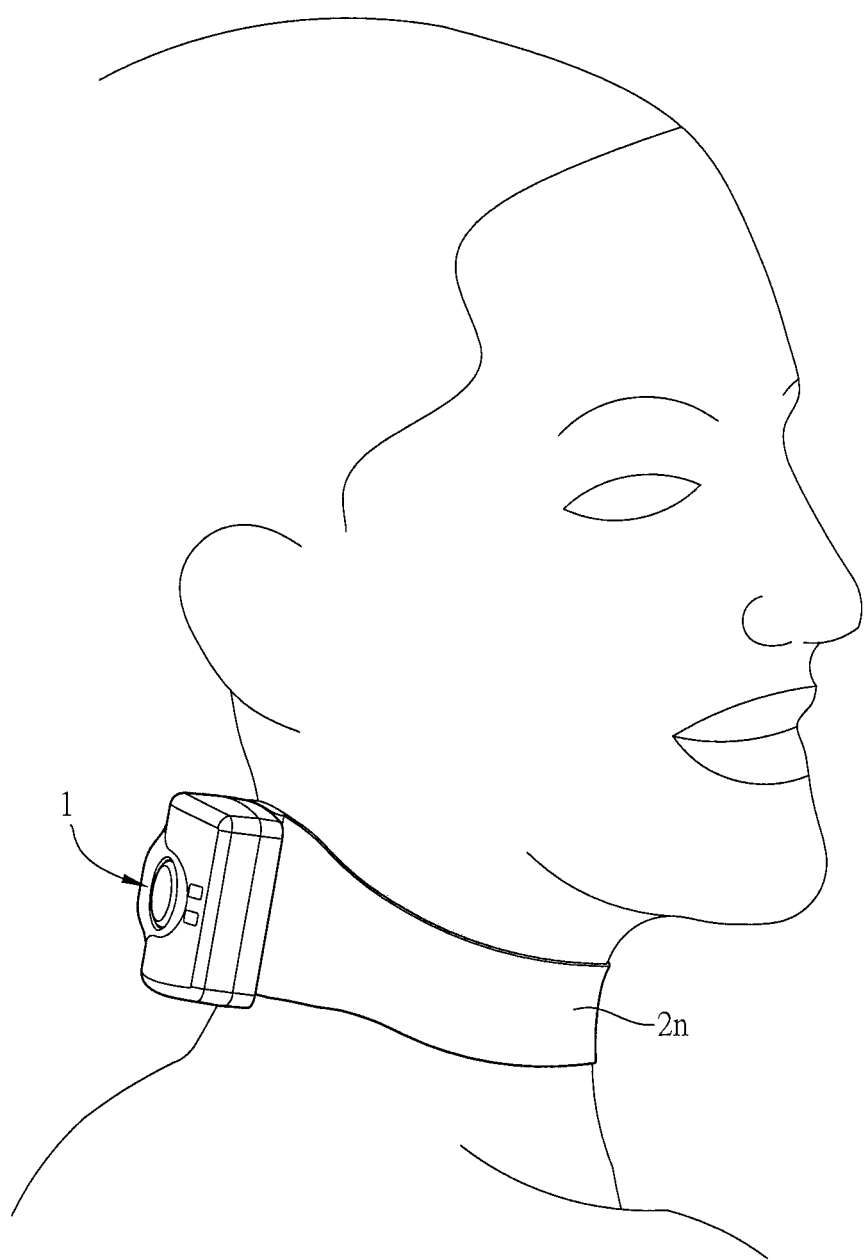
FIG. 3 is a schematic diagram showing a nerve electrical stimulation device according to another embodiment of this disclosure, which is applied to the neck of an individual.
Figure 4:
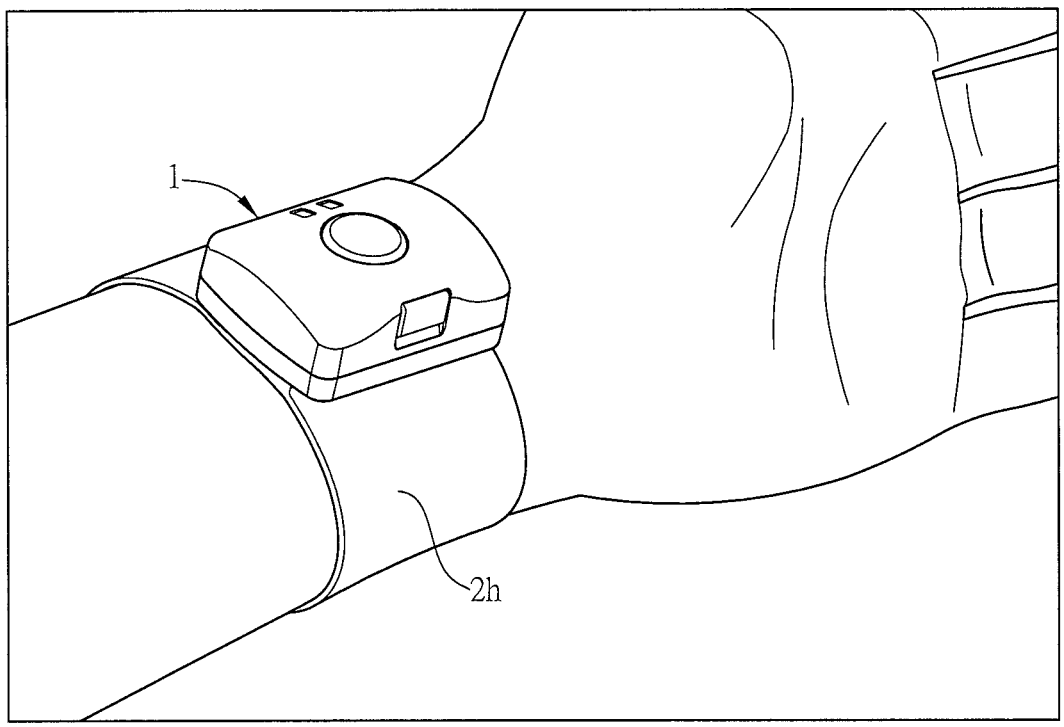
FIG. 4 is a schematic diagram showing a nerve electrical stimulation device according to another embodiment of this disclosure, which is applied to the wrist of an individual.

FIG. 3 is a schematic diagram showing a nerve electrical stimulation device according to another embodiment of this disclosure, which is applied to the neck of an individual, and FIG. 4 is a schematic diagram showing a nerve electrical stimulation device according to another embodiment of this disclosure, which is applied to the wrist of an individual.

Referring to FIGS. 3 and 4, the nerve electrical stimulation device 3 can be attached to different parts such as head, hand (elbow or wrist) or foot (angle or knee) of an individual by different magnetic electrode assemblies (e.g. the magnetic electrode assembly 2n for neck and the magnetic electrode assembly 2h for wrist). The magnetic electrode assemblies 2n and 2h both have a flexible main body. When being attached to different parts of the individual, the magnetic electrode assembly can fit the shape or curvature of the target region of the neck, hand or other parts of the individual. Accordingly, the electrical stimulation device can fit different curvatures or deflection of different parts of body by utilizing different magnetic electrode assemblies 2n or 2h. Moreover, the conductive gel is applied under the electrodes, so that the electrical stimulation device can be attached to the body surface of an individual. According to the above technical solutions, it is not needed to design different housings, magnetic electrical stimulation assemblies, or electrical stimulators for different parts to be treated. This configuration can relieve pains, make the operation more comfortable, and reduce the manufacturing and/or consumption cost.

In summary, the nerve electrical stimulation device of this disclosure includes an electrical stimulator and a magnetic electrode assembly. The electrical stimulator and the magnetic electrode assembly are mechanically connected by the magnetic attraction of the first magnetic unit and the second magnetic unit so as to form a mechanical connection route, so that the magnetic electrode assembly can be detachably positioned at one side of the electrical stimulator. Accordingly, the same electrical stimulator can be cooperated with various modes of magnetic electrode assemblies for applying to different parts of an individual. This design can save the manufacturing and/or consumption cost. In addition, the electrical stimulator and the magnetic electrode assembly are coupled through the first electrical connecting elements and the second electrical connecting elements, so that the electrical signals generated by the circuit board can be transmitted to the electrodes so as to form an electrical transmission route, which is different from the mechanical connection route. Therefore, the mechanical design and the electrical transmission design are not interfered and affected by each other, thereby increasing the freedom of design.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. A transcutaneous nerve electrical stimulation device, comprising:
    a transcutaneous electrical stimulator, comprising:
        a housing comprising an accommodating space,
        a circuit board disposed in the accommodating space,
        at least two first electrical connecting elements disposed on the circuit board, wherein one end of each first electrical connecting element is electrically connected to the circuit board, and the other end of each first electrical connecting element exposes from the housing, and
        at least a first magnetic unit disposed in the accommodating space; and
    a magnetic electrode assembly, comprising:
        a main body,
        two electrodes disposed on a surface of the main body opposite to the housing, wherein the electrodes are electrically connected to the circuit board and are configured to be disposed on a skin,
        at least a second magnetic unit disposed on the main body and located corresponding to the first magnetic unit, and
        at least two second electrical connecting elements passing through the main body and electrically connected to the electrodes, respectively, wherein the second electrical connecting elements are electrically connected to the other ends of the first electrical connecting elements, respectively, so that the first electrical connecting elements and the second electrical connecting elements form an electrical connecting route;
    wherein the magnetic electrode assembly is detachably positioned at one side of the transcutaneous electrical stimulator by a magnetic attraction of the first magnetic unit and the second magnetic unit.

2. The transcutaneous nerve electrical stimulation device according to claim 1, wherein the magnetic electrode assembly further comprises at least a substrate connecting to the main body, and the electrodes are disposed at one side of the substrate opposite to the main body.

3. The transcutaneous nerve electrical stimulation device according to claim 1, wherein the magnetic electrode assembly further comprises at least a conductive paste disposed one side of the electrode away from the main body.

4. The transcutaneous nerve electrical stimulation device according to claim 1, wherein the transcutaneous electrical stimulator outputs an electrical stimulation signal, the electrical stimulation signal is transmitted to the electrodes so as to generate an electric field between the electrodes to cover a target region, and an intensity of the electric field covering the target region is between 100V/m and 1000V/m.

5. The transcutaneous nerve electrical stimulation device according to claim 4, wherein a frequency range of the electrical stimulation signal is between 200 KHz and 1000 KHz.

6. The transcutaneous nerve electrical stimulation device according to claim 1, wherein each of the electrodes is a thin-film electrode.

7. The transcutaneous nerve electrical stimulation device according to claim 1, wherein the electrical connecting route is different from a magnetic attraction route formed by the first magnetic unit and the second magnetic unit.

8. The transcutaneous nerve electrical stimulation device according to claim 1, wherein the housing comprises an upper housing and a lower housing, the lower housing has a depression portion, the main body has a protrusion portion corresponding to the depression portion, the depression portion is engaged with the protrusion portion, and the second electrical connecting element penetrates through the protrusion portion of the main body.

9. The transcutaneous nerve electrical stimulation device according to claim 8, wherein the main body has an opening, and the lower housing is partially protruded beyond the opening.

10. The transcutaneous nerve electrical stimulation device according to claim 1, wherein the transcutaneous electrical stimulator further comprises:
- a prompt unit electrically connected to the circuit board and generating a prompt signal, wherein the prompt unit comprises a LED indicator, a vibration unit or a speaker.

11. The transcutaneous nerve electrical stimulation device according to claim 1, wherein when the magnetic electrode assembly is positioned at one side of the transcutaneous electrical stimulator by the magnetic attraction of the first magnetic unit and the second magnetic unit, the first electrical connecting elements contact the second electrical connecting elements.

* * * * *